United States Patent
Ishida et al.

[11] Patent Number: 5,543,409
[45] Date of Patent: Aug. 6, 1996

[54] INDANE DERIVATIVES FOR TREATING ENDOTOXIN SHOCK AND/OR NEPHRITIS

[75] Inventors: Akihiko Ishida, Urawa; Koichi Homma, Tokyo-to; Michihisa Yato, Urawa; Shinsuke Nishiyama; Fumikazu Okumura, both of Ohmiya, all of Japan

[73] Assignee: Tanabe Seiyaku Co., Ltd., Osaka, Japan

[21] Appl. No.: 445,202

[22] Filed: May 23, 1995

Related U.S. Application Data

[62] Division of Ser. No. 365,289, Dec. 28, 1994.

[30] Foreign Application Priority Data

Dec. 28, 1993 [JP] Japan .................... 5-333967

[51] Int. Cl.⁶ .................................. A61K 31/50
[52] U.S. Cl. .................................. 514/247
[58] Field of Search .............................. 514/247

[56] References Cited

U.S. PATENT DOCUMENTS 4,820,705 4/1989 Nickl et al. ............... 514/247

FOREIGN PATENT DOCUMENTS

| | | |
|---|---|---|
| 5461286 | 3/1986 | Australia . |
| 0194548 | 3/1986 | European Pat. Off. . |
| 0589037 | 9/1992 | European Pat. Off. . |
| 0579059 | 1/1994 | European Pat. Off. . |
| 23853 | 4/1989 | Japan . |
| 9215558 | 9/1992 | WIPO . |

*Primary Examiner*—Marianne M. Cintins
*Assistant Examiner*—Phyllis G. Spivack
*Attorney, Agent, or Firm*—Birch, Stewart, Kolasch & Birch, LLP

[57] ABSTRACT

Disclosed are indane compounds represented by the formula:

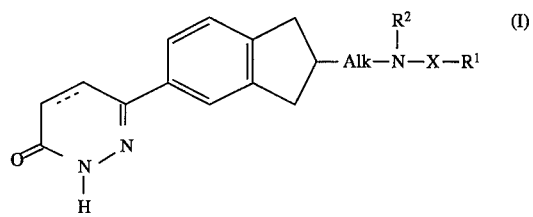

wherein $R^1$ is aryl, lower alkyl, cycloalkyl, halogeno-lower alkyl, lower alkenyl, phenyl-substituted lower alkenyl, monocyclic or bicyclic aromatic heterocyclic having N, O or S as a hetero atom, lower alkoxy, phenoxy, lower alkylamino, lower alkenylamino, phenylamino, lower alkyl substituted by monocyclic or bicyclic aromatic heterocyclic having N, O or S as a hetero atom, or lower alkenyloxy; $R^2$ is H or lower alkyl; X is carbonyl or thiocarbonyl; Alk is single bonding arm or lower alkylene; and the dotted line is presence or absence of a double bond, for treating endotoxin shock and/or nephritis.

19 Claims, No Drawings

INDANE DERIVATIVES FOR TREATING ENDOTOXIN SHOCK AND/OR NEPHRITIS

This application is a divisional of copending application Ser. No. 08/365,289, filed on Dec. 28, 1994, the entire contents of which are hereby incorporated by reference.

BACKGROUND OF THE INVENTION

This invention relates to novel indane derivatives having actions of protecting from endotoxin shock and/or actions of curing nephritis, processes for preparing the same and a synthetic intermediate of the same.

In Japanese Provisional Patent Publication No. 23853/1988, it has been disclosed that benzenesulfonamidindanyl compounds such as 6-(2-benzenesulfonamido-indan-5-yl)-4,5-dihydro-pyridazin-3(2H)-one exhibit antithrombotic actions. In PCT Provisional Patent Publication No. WO92/15558, it has been disclosed that benzenesulfonaminoalkylindane derivatives such as 6-[2-[(4-chlorophenyl)sulfonylaminomethyl]indan-5-yl]-3-oxo-2,3,4,5-tetrahydropyridazine have antagonistic actions on thromboxane $A_2$.

On the other hand, as an agent for curing endotoxin shock which occurs in a patient seriously infected with gram-negative bacteria, there have been conventionally used steroid hormones, aprotinin (a protease inhibitor) and dobutamine (a cardiac).

Further, as an agent for curing nephritis, there have been conventionally used prednisolon (asteroid agent), cyclophosphamide (an immunosuppressant), dipyridamole, dilazep (antiplatelets) and haperin (an anticoagulant).

SUMMARY OF THE INVENTION

An object of the present invention is to provide novel indane derivatives having excellent actions of protecting from endotoxin shock and/or excellent actions of curing nephritis, processes for preparing the same and a synthetic intermediate of the same.

That is, the present invention is concerned with an indane derivative represented by the formula (I):

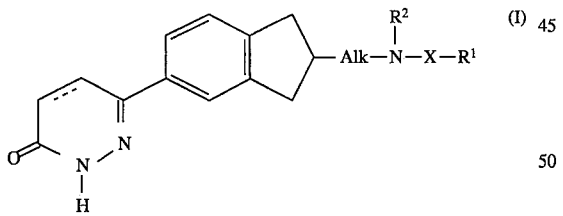

wherein $R^1$ represents a substituted or unsubstituted aryl group, a lower alkyl group, a cycloalkyl group, a halogeno-lower alkyl group, a lower alkenyl group, a phenyl-substituted lower alkenyl group, a substituted or unsubstituted monocyclic or bicyclic aromatic heterocyclic group having nitrogen atom, oxygen atom or sulfur atom as a hetero atom, a lower alkyl group which is substituted by a substituted or unsubstituted monocyclic or bicyclic aromatic heterocyclic group having nitrogen atom, oxygen atom or sulfur atom as a hetero atom, a substituted or unsubstituted lower alkoxy group, phenoxy group, a lower alkylamino group, a lower alkenylamino group, phenylamino group or a lower alkenyloxy group; $R^2$ represents hydrogen atom or a lower alkyl group; X represents carbonyl group or thiocarbonyl group; Alk represents a single bonding arm or a lower alkylene group; and the dotted line represents presence or absence of a double bond,
or a pharmaceutically acceptable salt thereof.

DESCRIPTION OF THE PREFERRED EMBODIMENTS

In the following, the present invention is explained in detail. In the desired compound (I) of the present invention, as the substituted or unsubstituted aryl group, there may be mentioned, for example, a phenyl group which may be substituted by 1 to 3 groups selected from the group consisting of a lower alkoxy group, a phenyl-substituted lower alkoxy group, a halogen atom, hydroxyl group, trifluoromethyl group, nitro group, a lower alkyl group and a di-lower alkylamino group. As the halogeno-lower alkyl group, there may be mentioned, for example, trifluoromethyl group. As the phenyl-substituted lower alkenyl group, there may be mentioned, for example, styryl group. As the substituted or unsubstituted monocyclic or bicyclic aromatic heterocyclic group having nitrogen atom, oxygen atom or sulfur atom as a hetero atom, there may be mentioned, for example, pyridyl group, furyl group, thienyl group, pyrazyl group, pyrimidyl group, quinolyl group and isoquinolyl group each of which may be substituted by 1 to 4 groups selected from the group consisting of a lower alkyl group, a halogeno-lower alkyl group, a lower alkoxy group, a lower alkylthio group, hydroxy group, mercapto group, cyano group, amino group, a substituted amino group (for example, a lower alkylamino group, a di-lower alkylamino group or an acylamino group), a halogen atom, phenoxy group, carboxyl group, a lower alkoxycarbonyl group, a lower alkylcarbonyloxy group, a lower alkylcarbonyl group, carbamoyl group and a di-lower alkylcarbamoyl group. As the lower alkyl group which is substituted by a substituted or unsubstituted monocyclic or bicyclic aromatic heterocyclic group having nitrogen atom, oxygen atom or sulfur atom as a hetero atom, there may be mentioned, for example, pyridylmethyl group. As the substituted or unsubstituted lower alkoxy group, there may be mentioned a lower alkoxy group which may be substituted by phenyl group.

As preferred examples of the compound of the present invention, there may be mentioned a compound which have a characteristic as follows;

(1A) $R^1$ is pyridyl group which may be substituted by 1 or 2 groups selected from the group consisting of a lower alkyl group, a halogeno-lower alkyl group, a lower alkoxy group, a lower alkylthio group, hydroxy group, mercapto group, cyano group, amino group, a substituted amino group (for example, a lower alkylamino group, a di-lower alkylamino group or an acylamino group), a halogen atom, phenoxy group, carboxyl group, a lower alkoxycarbonyl group, a lower alkylcarbonyloxy group, a lower alkylcarbonyl group, carbamoyl group and a di-lower alkylcarbamoyl group; a pyridyl-substituted lower alkyl group; a lower alkyl group; a cycloalkyl group; a lower alkenyl group; or a lower alkoxy group.

(1B) $R^1$ is pyridyl group which may be substituted by 1 or 2 groups selected from the group consisting of a lower alkyl group and amino group; a lower alkyl group; a lower alkenyl group; or a lower alkoxy group.

(1C) $R^1$ is pyridyl group which may be substituted by 1 or 2 groups selected from the group consisting of methyl group and amino group.

Besides, when $R^1$ is "pyridyl group which may be substituted", there is no limitation of the position of substituent(s) or position of linkage to the moiety -X- on the pyridine ring. However, as a preferred example, there may be mentioned a substituted or unsubstituted pyridyl group which is linked to the moiety -X- on 3-position of pyridine ring (i.e., a substituted or unsubstituted pyridin-3-yl group). In case of a substituted pyridyl group, there may be mentioned a 2- or 4-substituted or 2,4-di-substituted pyridin-3-yl group. As a more preferred example, there may be mentioned an unsubstituted pyridin-3-yl group or 2-substituted pyridin-3-yl group.

As another preferred example of the compound, there may be mentioned a compound which have a characteristic as follows;

(2) X is carbonyl group.

As another preferred example of the compound, there may be mentioned a compound which have a characteristic as follows;

(3) Alk is a lower alkylene group.

As another preferred example of the compound, there may be mentioned a compound which have a characteristic as follows;

(4) The dotted line represents presence of a double bond.

As a further preferred example of the compound, there may be mentioned a compound which have both characteristics of (1A) and (2) mentioned above.

As another preferred example of the compound, there may be mentioned a compound which have both characteristics of (2) and (4) mentioned above.

As a more preferred example of the compound, there may be mentioned a compound which have all characteristics of (1B), (2), (3) and (4) mentioned above.

As a particularly preferred example of the compound, there may be mentioned a compound which have all characteristics of (1C), (2), (3) and (4) mentioned above.

In the desired compound (I) of the present invention, two kinds of optical isomers based on an asymmetric carbon atom exist. Both of these optical isomers and a mixture thereof are included in the present invention.

The desired compound (I) of the present invention can be used for medical purposes either in a free form or in the form of a pharmaceutically acceptable salt thereof. As the pharmaceutically acceptable salt, there may be mentioned inorganic acid salts such as hydrochloride, phosphate and hydrobromide, and organic acid salts such as acetate, succinate, fumarate and methanesulfonate.

The desired compound (I) of the present invention can be administered either orally or parenterally, and it can be used as a medical preparation by mixing it with an excipient suitable for oral or parenteral administration. The medical preparation may be a solid preparation such as a tablet, a capsule and a powder, or a liquid preparation such as a solution, a suspension and an emulsion. Further, when the desired compound (I) is administered parenterally, it can be used in the form of an injection.

The dose varies depending on age, body weight and state of a patient and disease conditions of a patient, but, in general, the dose per day is preferably 1 to 300 mg/kg, particularly 3 to 100 mg/kg in the case of oral administration, and it is preferably 0.01 to 50 mg/kg, particularly 0.1 to 20 mg/kg in the case of parenteral administration.

According to the present invention, the desired compound (I) or a pharmaceutically acceptable salt thereof can be prepared by the following preparation processes (A) to (C).

(A) The desired compound (I) or a pharmaceutically acceptable salt thereof can be prepared by reacting a compound represented by the formula (II):

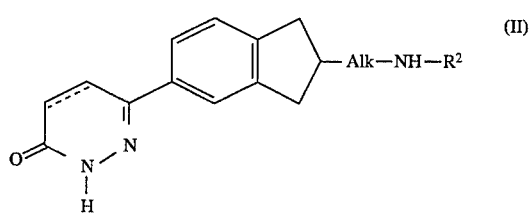

wherein $R^2$, Alk and the dotted line have the same meanings as defined above, or a salt thereof, with a compound represented by the formula (III):

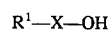

wherein $R^1$ and X have the same meanings as defined above, a salt thereof or a reactive derivative thereof and, if necessary, converting the resulting compound into a pharmaceutically acceptable salt thereof.

(B) Among the desired compounds (I), a compound represented by the formula (I-a):

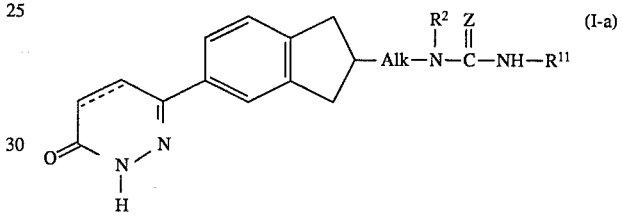

wherein $R^{11}$ represents a lower alkyl group, a lower alkenyl group or phenyl group; Z represents oxygen atom or sulfur atom; and $R^2$, Alk and the dotted line have the same meanings as defined above, or a pharmaceutically acceptable salt thereof can be prepared by reacting the starting compound (II) as shown above or a salt thereof, with a compound represented by the formula (IV):

wherein $R^{11}$ and Z have the same meanings as defined above, and, if necessary, converting the resulting compound into a pharmaceutically acceptable salt thereof.

(C) Among the desired compounds (I), a compound in which the dotted line represents presence of a double bond, i.e., a compound represented by the formula (I-b):

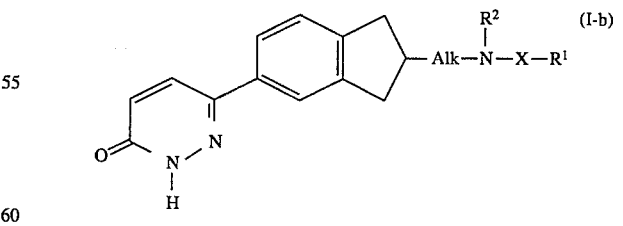

wherein $R^1$, $R^2$, X and Alk have the same meanings as defined above, or a pharmaceutically acceptable salt thereof can be prepared by oxidizing a compound in which the dotted line represents absence of a double bond among the desired compounds (I), i.e., a compound represented by the formula (I-c):

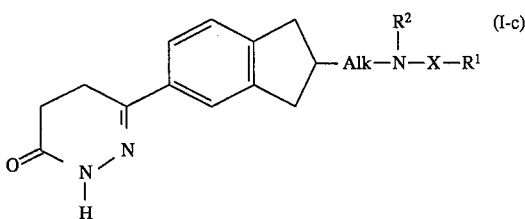

wherein $R^1$, $R^2$, X and Alk have the same meanings as defined above, and, if necessary, converting the resulting compound into a pharmaceutically acceptable salt thereof.

In Preparation process (A) described above, when the compound (I) is prepared by using the compound (III) or a salt thereof, the reaction can be carried out in a suitable solvent in the presence of a condensing agent.

As the condensing agent, there may be used commonly used condensing agents such as 1,3-dicyclohexylcarbodiimide, carbonyldiimidazole, 1-ethyl-3-(3'-dimethylaminopropyl)-carbodiimide and diethyl cyanophosphonate. As the salt of the compound (III), there may be used conventionally used salts such as an alkali metal salt, an alkaline earth metal salt and an organic amine salt. It is preferred that the above salt is previously converted into a free compound and the free compound is provided for the reaction with the compound (II).

In Preparation process (A), when the compound (I) is prepared by using a reactive derivative of the compound (III), the reaction can be suitably carried out in a suitable solvent in the presence or absence of an acid receptor. As the reactive derivative, there may be used reactive derivatives commonly used for condensation, such as acid halides (including halogenoformate), mixed acid anhydrides and active esters. As the acid receptor, there may be mentioned alkali metal carbonates such as potassium carbonate and sodium carbonate; alkali metal hydrogen carbonates such as potassium hydrogen carbonate and sodium hydrogen carbonate; alkali metal hydroxides such as sodium hydroxide and potassium hydroxide; tri-lower alkylamines such as triethylamine, tributylamine and diisopropylethylamine; tertiary amines such as 1,4-diazabicyclo[2.2.2]-octane, 1,5-diazabicyclo[4.3.0]non-5-ene, 1,8-diazabicyclo-[5.4.0]undec-7-ene; and aromatic amines such as pyridine, lutidine, collidine and dimethylaniline.

In Preparation process (B), the reaction of the compound (II) with the compound (IV) can be carried out easily by, for example, mixing the compound (II) and the compound (IV) in the presence or absence of a solvent according to a conventional method.

The solvent to be used in Preparation process (A) and Preparation process (B) described above may be any inert solvent which does not exert bad influence on either of the reactions of Preparation processes, and there may be mentioned, for example, halogen type solvents such as chloroform, dichloromethane and dichloroethane; aromatic hydrocarbons such as toluene and xylene; ether type solvents such as tetrahydrofuran, dioxane, diethyl ether and 1,2-dimethoxyethane; ketone type solvents such as acetone and methyl ethyl ketone; ester type solvents such as ethyl acetate; alcohol type solvent such as 2-methoxyethanol, 2-propanol and tert-butanol; acetonitrile; pyridine; 2,6-lutidine; dimethylformamide; dimethyl sulfoxide; 1,3-dimethyl-2-imidazolidinone; mixtures of these solvents; and a combination of these solvents and water.

Preparation processes (A) and (B) can be carried out under cooling to under heating, preferably, for example, at −30° C. to 150° C., particularly at −10° C. to room temperature.

The oxidation in Preparation process (C) can be carried out according to a conventional method, preferably, for example, by treating the compound (I-c) with sodium 3-nitrobenzenesulfonate in a suitable solvent under basic conditions; subjecting it to oxidation by using dimethyl sulfoxide in hydrogen bromide-acetic acid under acidic conditions; or halogenating it with bromide, chloride or the like and then subjecting the halogenated compound to dehydrohalogenation.

As the solvent, there may be used suitably water, acetic acid, propionic acid, trifluoroacetic acid, methanesulfonic acid and a hydrogen bromide-acetic acid solution.

In the reactions of the present invention, by using an optical isomer as the starting compound (II) or (I-c), a corresponding optically active desired compound (I), (I-a) or (I-b) can be obtained without racemization.

Among the starting compounds (II) of the present invention, a compound in which $R^2$ represents hydrogen atom, Alk represents a single bonding arm and the dotted line represents absence of a double bond has been described in Japanese Provisional Patent Publication No. 23853/1988. However, compounds other than the above compound are novel and can be prepared by reacting a compound represented by the formula (V):

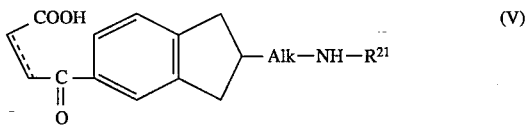

wherein $R^{21}$ represents hydrogen atom or a lower alkyl group and Alk and the dotted line have the same meanings as defined above, with hydrazine, if necessary, further alkylating the amino group of the resulting compound, for example, by reductive alkylation with the corresponding aldehyde compounds in the presence of appropriate reducing agent such as sodium borohydride ($NaBH_4$), sodium triacetoxyborohydride ($NaB(OCOCH_3)_3H$) when $R^{21}$ represents hydrogen atom and, if necessary, oxidizing the resulting compound when the dotted line represents absence of a double bond.

In the above reaction, the reaction of the compound (V) with hydrazine can be suitably carried out in the presence or absence of a suitable solvent. The solvent may be any inert solvent which does not exert bad influence on the reaction and include, for example, lower alcohols such as methanol and ethanol; lower aliphatic acids such as acetic acid and propionic acid; aromatic hydrocarbons such as toluene and xylene; and ethers such as tetrahydrofuran and dioxane. The reaction can be carried out at a wide range of temperature from room temperature to a boiling point of a reaction mixture, preferably, for example, 10° C. to 200° C., particularly 20° C. to 150° C.

The oxidation can be carried out in the same manner as in the oxidation of Preparation process (C) described above.

The starting compound (V) can be prepared by, for example, if necessary, after protecting an amino group of a compound represented by the formula (VI):

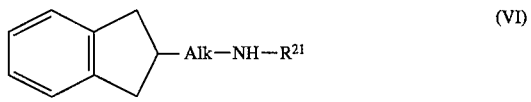

wherein $R^{21}$ and Alk have the same meanings as defined above, reacting said compound with a compound represented by the formula (VII):

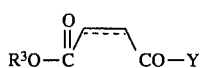

$$\text{R}^3\text{O}-\overset{\overset{\displaystyle O}{\|}}{\text{C}} \quad \text{CO}-\text{Y} \qquad \text{(VII)}$$

wherein $R^3$ represents an ester residue; Y represents a halogen atom; and the dotted line has the same meaning as defined above, and then removing the ester residue and/or the protective group from the resulting compound, or a method described below in Examples.

In the present specification, the lower alkyl group includes those having 1 to 6 carbon atoms, preferably 1 to 4 carbon atoms, particularly 1 to 3 carbon atoms. The lower alkoxy group includes those having 1 to 6 carbon atoms, preferably 1 to 4 carbon atoms. The lower alkylene group includes those having 1 to 10 carbon atoms, preferably 1 to 6 carbon atoms, particularly 1 to 4 carbon atoms. The lower alkenyl group includes those having 2 to 7 carbon atoms, particularly 2 to 5 carbon atoms. The cycloalkyl group includes those having 3 to 6 carbon atoms.

In the present specification, the substituted amino group includes not only a lower alkylamino group, a di-lower alkylamino group, acylamino group, N-lower alkyl-N-lower alkoxycarbonylamino group, N-lower alkyl-N-carbamoylamino group, N-lower alkyl-N-thiocarbamoylamino group (the said carbamoyl group or thiocarbamoyl group may be substituted by 1 or 2 groups of a lower alkyl group at the nitrogen atom), a lower alkylcarbamoyl group, but also those of which two substituents on amino group are combined together to form a ring such as pyrrolidino group, piperidino group, perhydroazepin-1-yl group, morpholino group, thiomorpholino group, piperazino group which may be substituted by a group selected from a lower alkyl group, a lower alkenyl group, acyl group, aryl group, etc. at the nitrogen atom of the 4-position. The acyl group includes formyl group, an alkylcarbonyl group and an alkoxycarbonyl group.

The lower alkyl group, lower alkoxy group, lower alkylene group and lower alkenyl group include straight ones and branched ones.

EXAMPLES

The present invention is described in detail by referring to Examples and Test examples, but the present invention is not limited thereby. In Example 1 to Example 10 and Example 92 to Example 104, starting compounds are described, and in Example 11 to Example 91 and Example 105 to Example 159, desired compounds are described.

Test Example 1

(Action of protecting mouse from death induced by endotoxin)

To ddy strain male mice (one group: 10 mice) which had fasted for about 24 hours, each test sample dissolved or suspended in a 0.25% sodium carboxymethyl cellulose (CMC) aqueous solution was orally administered (100 mg/kg). After 30 minutes, 100 mg/10 ml/kg of endotoxin (lipopolysaccharide) derived from Escherichia coli dissolved in physiological saline was administered intraperitoneally. When the survival rate of the control group to which the CMC aqueous solution had been orally administered became 20% (about 20 hours after administration of endotoxin), the survival rates of the groups to which the test samples had been administered were determined. The results are shown in Table 1.

TABLE 1

| Compound tested[*] (Example No.) | Survival rate (%) |
|---|---|
| 11 | 100 |
| 12 | 90 |
| 18 | 80 |
| 22 | 70 |
| 25 | 80 |
| 35 | 80 |
| 37 | 60 |

[*]The compounds obtained in Examples described below were used as compounds to be tested in the experiment.

Test Example 2

(Action on rat glomerular nephritis)

Rabbits were immunized several times with a renal glomerular basement membrane fraction obtained from WKY strain rats and an adjuvant. Thereafter, blood was collected to obtain a nephrotoxic serum (NTS). This NTS was diluted by 50 times with physiological saline, and the diluted NTS was once administered intravenously to male WKY rats of 8 weeks old in a dose of 2.5 ml per 1 kg of body weight to induce nephritis. In normal group of rats, the same volume of physiological saline was intravenously administered.

In the experiment, one group consisted of 6 rats, and each compound to be tested was suspended in water with small amount of Tween 80 (trade name, produced by Nacalai Tesque Co.), and was orally administered to the test group of rats at a dose of 30 mg/kg/10 ml twice a day for 8 days. In normal group and control group of rats, the same volume of water was orally administered instead of the test compound. After 7 days, the rats were placed in metabolic cages and urine was collected for 24 hours. Concentrations of protein in urine were measured by the sulfosalicylic acid method to determine amounts of protein excreted in the urine (mg/day). The inhibition rate of excretion of protein were calculated by the following equation.

$$\text{Inhibition rate (\%)} = 100 - \frac{\begin{pmatrix}\text{amount of excreted protein in test group}\end{pmatrix} - \begin{pmatrix}\text{amount of excreated protein in normal group}\end{pmatrix}}{\begin{pmatrix}\text{amount of excreted protein in control group}\end{pmatrix} - \begin{pmatrix}\text{amount of excreated protein in normal group}\end{pmatrix}} \times 100$$

The results are shown in Table 2. As seen in Table 2, inhibition rate of the protein excretion of the group which had been administered the test compound was about 60 to 99%.

TABLE 2

| Compound tested[*] (Example No.) | Inhibition rate (%) |
|---|---|
| 40 | 72.4 |
| 48 | 60.3 |
| 60 | 59.5 |
| 63 | 61.6 |
| 105 | 60.2 |
| 106 | 81.0 |
| 109 | 67.4 |

TABLE 2-continued

| Compound tested*) (Example No.) | Inhibition rate (%) |
| --- | --- |
| 110 | 91.8 |
| 127 | 93.0 |
| 129 | 98.9 |
| 148 | 88.9 |

*)The compounds obtained in Examples described below were used as compounds to be tested in the experiment.

Example 3

Iodotrimethylsilane (9 ml) was added to 13.16 g of 2-(N-methoxycarbonyl-N-propylamino)-5-[4,5-dihydropyridazin-3(2H)-on-6-yl]indane dissolved in 130 ml of chloroform. The mixture was refluxed under heating for 2 hours. After cooling, aqueous ammonia was added to the solution. The organic layer was collected by separation, washed with water and dried, and the solvent was removed. The resulting crude crystals were recrystallized from acetone to obtain 7.78 g of 2-propylamino-5-[4,5-dihydropyridazin-3(2H)-on-6-yl]indane.

m.p.: 146° to 148° C.

Example 2

In 70 ml of a 25% hydrogen bromide-acetic acid solution was suspended 8.02 g of 2-amino-5-[4,5-dihydropyridazin-3(2H)-on-6-yl]indane, and 2.96 g of dimethyl sulfoxide was added to the suspension under ice cooling. The mixture was stirred at room temperature for 1.5 hours. Then, 140 ml of diethyl ether was added to the reaction mixture, and crystals precipitated were collected by filtration and recrystallized from methanol to obtain 8.55 g of 2-amino-5-[pyridazin-3(2H)-on-6-yl]indane·hydrobromide.

m.p.:>300° C.

Example 3

2-Propylamino-5-[4,5-dihydropyridazin-3(2H)-on-6-yl]indane was treated in the same manner as in Example 2 to obtain 2-propylamino-5-[pyridazin-3(2H)-on-6-yl]indane.

m.p.: 137° to 139° C.

Example 4

(1) To 48.3 g of methyl hydrogen succinate dissolved in 840 ml of dichloroethane were added 46.4 g of oxalyl chloride and 2 drops of dimethylformamide. The mixture was stirred at room temperature for 5 hours. Then, under ice cooling, 34.6 g of 2-(acetylaminomethyl)indane dissolved in 280 ml of dichloroethane and 97.6 g of anhydrous aluminum chloride were added to the reaction mixture. After the mixture was stirred for 1 hour, the reaction mixture was poured into ice water. The organic layer was collected by separation, washed with water and dried, and the solvent was removed to obtain 51.8 g of 2-(acetylamino) methyl-5-(3methoxycarbonylpropionyl) indane.

m.p.: 139° to 140° C.

(2) In 800 ml of 10N hydrochloric acid was suspended 51.8 g of the compound obtained, and the mixture was refluxed under heating overnight. After the reaction mixture was concentrated and cooled, precipitated crystals (48.5 g) were collected by filtration. The crystals were suspended in 300 ml of acetic acid, and 30 g of hydrazine monohydrate was added to the suspension. The mixture was refluxed under heating for 4 hours. After cooling, diethyl ether was added to the mixture, and crystals precipitated were collected by filtration. The crystals obtained were suspended in water, adjusted to pH 9 with a 10% sodium hydroxide aqueous solution and then extracted with chloroform. The organic layer was collected by separation, washed with water and dried, and the solvent was removed. The residue was recrystallized from methanol to obtain 35.3 g of 2-aminomethyl-5-[4, 5-dihydropyridazin-3(2H)-on-6-yl]indane.

m.p.: 170° to 171° C.

(3) In 20 ml of acetic acid was suspended 4.90 g of 2-aminomethyl-5-[4,5-dihydropyridazin-3(2H)-on-6-yl]indane, and 50 ml of 30% hydrogen bromide-acetic acid and 2.8 g of dimethyl sulfoxide were added to the suspension. The mixture was stirred for 3 hours. To the mixture was added 300 ml of isopropyl ether, and crystals precipitated were collected by filtration. The crude crystals obtained were recrystallized from methanol to obtain 5.11 g of 2-amino-methyl-5-[pyridazin-3(2H)-on-6-yl] indane·hydrobromide.

m.p.: >300° C.

Examples 5 and 6

By treating the corresponding starting compounds in the same manner as in Example 4-(1) and Example 4-(2), compounds shown in Table 3 were obtained.

TABLE 3

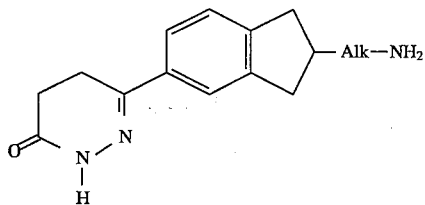

| Example No. | Alk | Physical properties |
| --- | --- | --- |
| 5 | $-(CH_2)_2-$ | m.p. 189 to 190° C. |
| 6 | $-(CH_2)_4-$ | m.p. 153 to 155° C. |

Examples 7 and 8

By treating the corresponding starting compounds in the same manner as in Example 4-(3), compounds shown in Table 4 were obtained.

TABLE 4

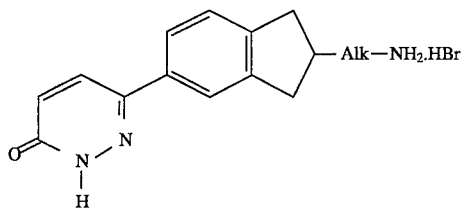

| Example No. | Alk | Physical properties |
| --- | --- | --- |
| 7 | $-(CH_2)_2-$ | m.p. 279 to 280° C. (decomposed) |
| 8 | $-(CH_2)_4-$ | m.p. 279 to 281° C. |

Example 9

(1) Propanal (1.51 g) dissolved in 5 ml of methanol was added dropwise to 6.15 g of 2-aminomethyl-5-[4,5-dihydropyridazin-3(2H)-on-6-yl]indane dissolved in 60 ml of methanol. The mixture was stirred at room temperature for 30 minutes. Then, under ice cooling, 1.03 g of sodium borohydride was added to the mixture. The resulting mixture was stirred at the same temperature for 20 minutes and then stirred at room temperature for 1 hour. After methanol was removed, water was added to the residue, and the residue was extracted with ethyl acetate. The organic layer was collected by filtration, washed with water and dried, and the solvent was removed. The residue was purified by silica gel column chromatography (solvent; chloroform: methanol (15:1)) to obtain 5.22 g of 2-propylaminomethyl-5-[4,5-dihydropyridazin-3(2H)-on-6-yl]indane.

m.p.: 82° to 84° C.

(2) 2-propylaminomethyl-5-[4,5-dihydropyridazin-3(2H)-on-6-yl]indane (5.08 g) was treated in the same manner as in Example 4-(3) to obtain 4.52 g of 2-propylaminomethyl-5[pyridazin-3(2H)-on-6-yl]indane·hydrobromide. Then, the compound obtained was treated with a 10% sodium hydroxide aqueous solution to obtain 3.13 g of 2-propylaminomethyl-5 -[pyridazin-3(2H)-on-6-yl]indane.

m.p.: 144° to 146° C.

Example 10

In the same manner as in Example 9-(1), 2-[2-propylaminoethyl]-5-[4,5-dihydropyridazin-3(2H)-on-6-Yl]indane was obtained from the corresponding starting compounds.

m.p.: 123° to 124° C.

Example 11

Butyryl chloride (4.09 g) dissolved in 20 ml of tetrahydrofuran was added dropwise to 7.26 g of 2-amino-5-[4,5-dihydropyridazin-3(2H)-on-6-yl]indane and 7.05 g of triethylamine suspended in 70 ml of 1,3-dimethyl-2-imidazolidinone. The mixture was stirred at room temperature for 4 hours. The reaction mixture was poured into ice water, and crystals precipitated were collected by filtration, washed with water and dried. The crystals were recrystallized from ethyl acetate to obtain 7.47 g of 2-butyrylamino-5 -[4,5-dihydropyridazin-3(2H)-on-6-yl]indane.

m.p.: 214° to 215° C.

Examples 12 to 28

By treating the corresponding starting compounds in the same manner as in Example 11, compounds shown in Tables 5 and 6 were obtained.

TABLE 5

| Example No. | $R^1$ | Physical properties |
| --- | --- | --- |
| 12 | —$C_2H_5$ | m.p. 218 to 219° C. |
| 13 | -n-$C_4H_9$ | m.p. 210 to 211° C. |
| 14 | —$CF_3$ | m.p. 236 to 237° C. |
| 15 | —$CH_2CH(CH_3)_2$ | m.p. 212 to 213° C. |
| 16 | cyclopropyl | m.p. 242 to 243 ° C. |
| 17 | —CH=$CH_2$ | m.p. 208 to 210° C. |
| 18 | 3-pyridyl | m.p. 229 to 230° C. |
| 19 | 3-thienyl | m.p. 246 to 249° C. |
| 20 | 3-furyl | m.p. 248 to 250° C. |
| 21 | phenyl | m.p. 263 to 265° C. |
| 22 | pyrazinyl | m.p. 232 to 235° C. |
| 23 | isoquinolinyl | m.p. 204 to 207° C. |
| 24 | quinolinyl | m.p. 178 to 180° C. |

TABLE 5-continued

[Structure: indane with NH—CO—R¹ substituent and dihydropyridazinone]

| Example No. | R¹ | Physical properties |
|---|---|---|
| 25 | [2-methylpyridyl] | m.p. 197 to 198° C. |

TABLE 6

[Structure: indane with N(R²)—CO—R¹ substituent and dihydropyridazinone]

| Example No. | R¹ | R² | Physical properties |
|---|---|---|---|
| 26 | [pyridyl] | -n-C$_3$H$_7$ | m.p. 150 to 152° C. |
| 27 | —CH=CH$_2$ | -n-C$_3$H$_7$ | m.p. 125 to 127° C. |
| 28 | -n-C$_3$H$_7$ | -n-C$_3$H$_7$ | m.p. 105 to 106° C. |

Example 29

Propyl isocyanate (2.38 g) was added dropwise to 5.13 g of 2-amino-5-[4,5-dihydropyridazin-3(2H)-on-6-yl]indane suspended in 60 ml of 2-methoxyethanol. The mixture was stirred at room temperature for 10 minutes. Crystals precipitated were collected by filtration and recrystallized from methanol-acetonitrile to obtain 4.91 g of 2(propylcarbamoyl) amino-5-[4,5-dihydropyridazin-3(2H)-on-6-yl]indane.

m.p.: 214° to 216° C.

Example 30

2-Amino-5-[4,5-dihydropyridazin-3(2H)-on-6-yl]indane and butyl isocyanate were treated in the same manner as in Example 29 to obtain 2-(butylcarbamoyl)amino-5-[4,5 -dihydropyridazin-3(2H)-on-6-yl]indane.

m.p.: 206° to 207° C.

Example 31

2-Amino-5-[4,5-dihydropyridazin-3(2H)-on-6-yl]indane and phenyl isocyanate were treated in the same manner as in Example 29 to obtain 2-(phenylcarbamoyl)amino-5-[4,5-dihydropyridazin-3(2H)-on-6-yl]indane.

m.p.: 249° to 251° C.

Examples 32 to 34

By treating 2-amino-5-[4,5-dihydropyridazin-3(2H)-on-6yl]indane and each corresponding isothiocyanate in the same manner as in Example 29, compounds shown in Table 7 were obtained.

TABLE 7

[Structure: indane with NH—CS—R¹ substituent and dihydropyridazinone]

| Example No. | R¹ | Physical properties |
|---|---|---|
| 32 | —NH-n-C$_3$H$_7$ | m.p. 199 to 200° C. |
| 33 | —NH-n-C$_4$H$_9$ | m.p. 165 to 167° C. |
| 34 | —NH—[phenyl] | m.p. 201 to 202° C. |

Example 35

Under ice cooling, 2.46 g of isobutyl chloroformate was added to 4.07 g of 2-propylamino-5-[4,5-dihydropyridazin3(2H)-on-6-yl]indane and 2.02 g of triethylamine dissolved in 40 ml of chloroform, and the mixture was stirred for 1 hour. The organic layer was washed with water and dried, and the solvent was removed. The resulting crude crystals were recrystallized from ethyl acetate to obtain 3.75 g of 2-(N,prolpyl-N-isobutoxycarbonylamino)-5-[4,5-dihydropyridazin-3(2H)-on-6-yl]indane.

m.p.: 161° to 162° C.

Examples 36 to 39

By treating the corresponding starting compounds in the same manner as in Example 35, compounds shown in Table 8 were obtained.

TABLE 8

[Structure: indane with N(R²)—CO—R¹ substituent and dihydropyridazinone]

| Example No. | R¹ | R² | Physical properties |
|---|---|---|---|
| 36 | —O—[phenyl] | -n-C$_3$H$_7$ | m.p. 174 to 175° C. |
| 37 | —O—CH$_2$—[phenyl] | -n-C$_3$H$_7$ | m.p. 115 to 117° C. |

TABLE 8-continued

| Example No. | R¹ | R² | Physical properties |
|---|---|---|---|
| 38 | —O-n-C₃H₇ | H | m.p. 173 to 175° C. |
| 39 | —O—CH=CH₂ | H | m.p. 205 to 206° C. |

Example 40

20 m of a 25% hydrogen bromide-acetic acid solution was added to 4.00 g of 2-butyrylamino-5-[4,5-dihydropyridazin-3(2H)-on-6-yl]indane suspended in 45 ml of acetic acid, and then 1.14 ml of dimethyl sulfoxide was added to the mixture. The resulting mixture was stirred at room temperature for 3.5 hours. Hydrogen bromide-acetic acid was removed, and the residue was recrystallized from hydrous ethanol to obtain 3.50 g of 2-butyrylamino-5-[pyridazin-3(2H)-on-6-yl]indane.

m.p.: 228° to 229° C.

Examples 41 to 48

By treating the corresponding starting compounds in the same manner as in Example 40, compounds shown in Table 9 were obtained.

TABLE 9

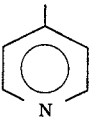

| Example No. | R¹ | R² | Physical properties |
|---|---|---|---|
| 41 | —C₂H₅ | H | m.p. 251 to 252° C. |
| 42 | ▷ (cyclopropyl) | H | m.p. 273 to 274° C. |
| 43 | —CH₂CH(CH₃)₂ | H | m.p. 238 to 240° C. |
| 44 | (4-pyridyl) | H | m.p. 263 to 265° C. |
| 45 | (4-pyridyl) | -n-C₃H₇ | m.p. 232 to 234° C. |

TABLE 9-continued

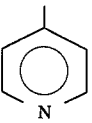

| Example No. | R¹ | R² | Physical properties |
|---|---|---|---|
| 46 | -n-C₃H₇ | -n-C₃H₇ | m.p. 166 to 167° C. |
| 47 | —NH-n-C₃H₇ | H | m.p. 235 to 236° C. |
| 48 | —O-n-C₃H₇ | H | m.p. 202 to 203° C. |

Example 49

Under ice cooling, 3.0 g of acryloyl chloride dissolved in 50 ml of tetrahydrofuran was added dropwise to a suspension of 5.03 g of 2-amino-5-[pyridazin-3(2H)-on-6-yl]indane·hydrobromide in 150 ml of ethyl acetate and 150 ml of water containing 4.52 g of potassium carbonate, and the mixture was stirred for 3 hours. Crystals precipitated were collected by filtration, washed with water, dried and then recrystallized from methanol-acetonitrile to obtain 3.69 g of 2-acryloylamino-5-[pyridazin-3(2H)-on-6-yl]indane.

m.p.: 235° to 237° C.

Example 50

2-Amino-5-[pyridazin-3(2H)-on-6-yl]indane·hydrobromide and vinyl chloroformate were treated in the same manner as in Example 49 to obtain 2-vinyloxycarbonylamino-5-[pyridazin-3(2H)-on-6-yl]indane.

m.p.: 205° to 206° C.

Example 51

Triethylamine (2.01 g) was added to 3.00 g of 2-propylamino-5-[pyridazin-3(2H)-on-6-yl]indane·hydrobromide suspended in 30 ml of dichloromethane, and the mixture was stirred for 20 minutes. Phenyl chloroformate (1.66 g) was added to the mixture, and the resulting mixture was stirred at room temperature for 2 hours. The organic layer was washed with water and dried, and the solvent was removed.

The resulting crude crystals were recrystallized from ethyl acetate and hexane to obtain 3.47 g of 2-(N-propyl-N-phenoxycarbonylamino)-5-[pyridazin-3-(2H)-on-6-yl]indane.

m.p.: 140° to 141° C.

Example 52

2-Propylamino-5-[pyridazin-3(2H)-on-6-yl]indane·hydrobromide and isobutyl chloroformate were treated in the same manner as in Example 51 to obtain 2-(N-propyl-N-isobutoxycarbonylamino)-5-[pyridazin-3(2H)-on-6-yl]indane.

m.p.,: 178° to 179° C.

Example 53

Triethylamine (2.0 g) was added to 60 ml of a suspension containing 5.04 g of 2-amino-5-[pyridazin-3(2H)-on-6yl]indane·hydrobromide suspended in 2-methoxyethanol, and the mixture was stirred for 10 minutes. Then, 2.33 g of propyl isothiocyanate was added dropwise to the mixture, and the resulting mixture was stirred at 50° C. for 7 hours. After cooling, 100 ml of water and 300 ml of isopropyl ether were added to the reaction mixture, and the resulting mixture was stirred. Crystals precipitated were collected by filtration, washed with water and dried. The crystals obtained were recrystallized from ethanol to obtain 4.53 g of 2-[(propyl)thiocarbamoyl]amino-5-[pyridazin-3(2H)-on-6yl]indane.

m.p.: 197° to 199° C.

Example 54

An aqueous solution (100 ml) containing 3.30 g of potassium carbonate dissolved in water was added to 100 ml of a suspension containing 3.50 g of 2-aminomethyl-5-[pyridazin3(2H)-on-6-yl]indane·hydrobromide suspended in ethyl acetate. Then, under ice cooling, 2.30 g of butyryl chloride dissolved in 30 ml of tetrahydrofuran was added to the mixture, and the resulting mixture was stirred for 3 hours. Crystals precipitated were collected by filtration, washed with water, dried and then recrystallized from methanol to obtain 2.75 g of 2-(butyrylamino)methyl-5-[pyridazin-3(2H)-on-6-yl]indane.

m.p.: 204° to 205° C.

Examples 55 to 64

By treating the corresponding starting compounds in the same manner as in Example 54, compounds shown in Tables 10 and 11 were obtained.

TABLE 10

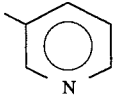

| Example No. | R¹ | Physical properties |
|---|---|---|
| 55 | —CH=CH₂ | m.p. 202 to 204° C. |
| 56 | cyclopropyl | m.p. 226 to 227° C. |
| 57 | —CH=CH—phenyl (E) | m.p. 238 to 240° C. |
| 58 | phenyl | m.p. 245 to 246° C. |
| 59 | thienyl | m.p. 247 to 248° C. |
| 60 | pyridyl | m.p. 193 to 194° C. |
| 61 | —O-n-C₃H₇ | m.p. 172 to 173° C. |

TABLE 11

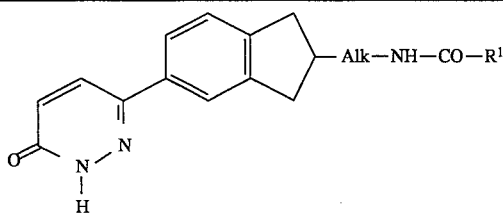

| Example No. | R¹ | Alk | Physical properties |
|---|---|---|---|
| 62 | —O—CH=CH₂ | —(CH₂)₂— | m.p. 181 to 182° C. |
| 63 | —CH=CH₂ | —(CH₂)₄— | m.p. 170 to 171° C. |
| 64 | —O—C₃H₇ | —(CH₂)₄— | m.p. 129 to 130° C. |

Example 65

Under ice cooling, 1.71 g of diethylphosphoryl cyanide was added to 80 ml of a suspension containing 3.06 g of 2-aminomethyl-5-[pyridazin-3(2H)-on-6-yl]indane·hydrobromide and 1.15 g of 3-methylcrotonic acid suspended in dimethylformamide, and then 20 ml of a solution containing 2.89 g of triethylamine dissolved in dimethylformamide was added dropwise to the mixture. The resulting mixture was stirred at the same temperature for 2.5 hours. The reaction mixture was poured into ice water, and crystals precipitated were collected by filtration. The crystals obtained were washed with water, dried and then recrystallized from ethyl acetate-methanol to obtain 2.45 g of 2-[(3-methylcrotonoyl)amino]methyl-5-[pyridazin-3(2H)-on-6-yl]indane.

m.p.: 204° to 205° C.

Example 66

Triethylamine (1.05 g) was added to 40 ml of a suspension containing 2.70 g of 2-aminomethyl-5-[pyridazin-3(2H)-on-6yl]indane·hydrobromide suspended in 2-methoxyethanol, and the mixture was stirred at room temperature for 10 minutes. To the mixture was added 1.10 g of allyl isocyanate, and the resulting mixture was stirred at room temperature for 1.5 hours. The reaction mixture was poured into ice water, and crystals precipitated were collected by filtration. The crystals obtained were washed with water, dried and then recrystallized from methanol to obtain 2.35 g of 2[(allylcabamoyl)amino]methyl-5-[pyridazin-3(2H)-on-6yl]indane.

m.p.: 208° to 209° C.

Example 67

The corresponding starting compound and propyl isothiocyanate were treated in the same manner as in Example 66 to obtain 2-{2-[(propyl)thiocarbamoyl]aminoethyl}-5-[pyridazin-3(2H)-on-6-yl]indane.

m.p.: 155° to 157° C.

Example 68

Triethylamine (1.47 g) was added to 15 ml of a suspension containing 1.57 g of 2-aminomethyl-5-[4,5-dihydropyridazin-3(2H)-on-6-yl]indane suspended in 1,3-dimethyl-2-imidazolidinone, and the mixture was stirred at room temperature for 10 minutes. Then, 0.83 g of butyryl chloride dissolved in 8 ml of tetrahydrofuran was added dropwise to the mixture, and the resulting mixture was stirred for 1 hour. The reaction mixture was poured into ice water, and crystals precipitated were collected by filtration. The crystals obtained were washed with water, dried and then recrystallized from ethyl acetate-methanol to obtain 1.47 g of 2-(butyrylamino)methyl-5-[4,5-dihydropyridazin-3(2H)-on-6-yl] indane.

m.p.: 172° to 173° C.

Examples 69 to 72

By treating the corresponding starting compounds in the same manner as in Example 68, compounds shown in Table 12 were obtained.

TABLE 12

| Example No. | $R^1$ | $R^2$ | Alk | Physical properties |
| --- | --- | --- | --- | --- |
| 69 | $-CH=CH_2$ | H | $-CH_2-$ | m.p. 198 to 200° C. |
| 70 | $-O\text{-}n\text{-}C_3H_7$ | H | $-CH_2-$ | m.p. 140 to 141° C. |
| 71 | $-n\text{-}C_3H_7$ | $-n\text{-}C_3H_7$ | $-(CH_2)_2-$ | m.p. 89 to 90° C. |
| 72 | $-O\text{-}n\text{-}C_3H_7$ | H | $-(CH_2)_4-$ | m.p. 110 to 111° C. |

Example 73

25 ml of 30% hydrogen bromide-acetic acid and 1 ml of dimethyl sulfoxide were added to 20 ml of a suspension containing 3.13 g of 2-(butyrylamino)methyl-5-[4,5-dihydropyridazin-3(2H)-on-6-yl]indane suspended in acetic acid. The mixture was stirred at room temperature for 3 hours. Diisopropyl ether was added to the mixture, and crystals precipitated were collected by filtration, washed with water, dried and then recrystallized from methanol to obtain 2.80 g of 2-(butyrylamino)methyl-5-[pyridazin-3(2H)-on- 6-yl]indane.

m.p.: 204° to 205° C.

Examples 74 to 77

By treating the corresponding starting compounds in the same manner as in Example 73, compounds shown in Table 13 were obtained.

TABLE 13

| Example No. | $R^1$ | $R^2$ | Alk | Physical properties |
| --- | --- | --- | --- | --- |
| 74 | $-CH=CH_2$ | H | $-CH_2-$ | m.p. 202 to 204° C. |
| 75 | $-O\text{-}n\text{-}C_3H_7$ | H | $-CH_2-$ | m.p. 172 to 173° C. |
| 76 | $-n\text{-}C_3H_7$ | $-n\text{-}C_3H_7$ | $-(CH_2)_2-$ | m.p. 122 to 124° C. |
| 77 | $-O\text{-}n\text{-}C_3H_7$ | H | $-(CH_2)_4-$ | m.p. 129 to 130° C. |

Examples 78 to 88

By treating the corresponding starting compounds in the same manner as in Example 11, compounds shown in Table 14 were obtained.

TABLE 14

| Example No. | $R^1$ | Physical properties |
| --- | --- | --- |
| 78 | 3,4,5-tri(OCH₃)phenyl | m.p. 225 to 226° C. |

TABLE 14-continued

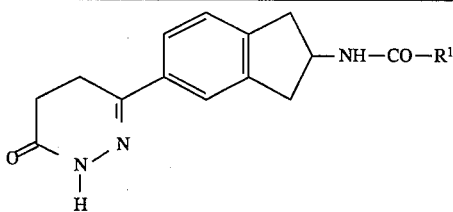

| Example No. | R¹ | Physical properties |
|---|---|---|
| 79 | -C₆H₄-Cl | m.p. 265 to 267° C. |
| 80 | -C₆H₄-OCH₃ | m.p. 227 to 229° C. |
| 81 | -C₆H₄-O(CH₂)₅CH₃ | m.p. 233 to 235° C. |
| 82 | -C₆H₄-OCH₂-C₆H₅ | m.p. 257 to 259° C. |
| 83 | -C₆H₄-OH | m.p. 298 to 300° C. |
| 84 | -C₆H₄-CF₃ | m.p. 243 to 246° C. |
| 85 | -C₆H₄-NO₂ | m.p. 222 to 225° C. |
| 86 | -C₆H₄-N(CH₃)₂ | m.p. 262 to 269° C. |
| 87 | -C₆H₄-(CH₂)₅CH₃ | m.p. 230 to 232° C. |
| 88 | -C₆H₄-O(CH₂)₄-C₆H₅ | m.p. 192 to 194° C. |

Example 89

(1) In 1,400 ml of ethanol was dissolved 8.41 g of 2-amino-5-[4,5-dihydropyridazin-3(2H)-on-6-yl]indane, and 8.52 g of (+)-camphorsulfonic acid was added to the solution. The resulting salts were recrystallized from ethanol several times to obtain 5.20 g of optically active 2-amino-5-[4,5-dihydropyridazin-3(2H)-on-6-yl]indane·(+)-camphorsulfonate.

m.p.: 256° to 257° C. (decomposed)

$[\alpha]_D^{20}$: −13.4° (c=1.00, H₂O)

(2) All mother liquor obtained in the above (1) was recovered and neutralized with a potassium carbonate aqueous solution, and ethanol was removed. After the residue was extracted with ethyl acetate, the solvent was removed. In 1,000 ml of ethanol was dissolved 5.23 g of the residue, and 5.29 g of (−)-camphorsulfonic acid was added to the solution. The resulting salts were recrystallized from ethanol several times to obtain 4.99 g of optically active 2-amino-5-[4,5-dihydropyridazin-3(2H)-on6-yl]indane·(−)-camphorsulfonate.

m.p.: 257° to 258° C. (decomposed)

$[α]_D^{20}$: +13.1° (c=1.00, $H_2O$)

(3) In 1.65 l of warm water was dissolved 138.8 g of optically active 2-amino-5-[4,5-dihydropyridazin-3(2H)-on6-yl]indane·(−)-camphorsulfonate. Under cooling, 13.05 g of sodium hydroxide dissolved in 130 ml of water was added dropwise to the solution, and the mixture was cooled for 2 hours. Crystals precipitated were collected by filtration, dried and then recrystallized from methanol to obtain 66.6 g of (+)-2-amino-5-[4, 5-dihydropyridazin-3(2H)-on-6-yl]indane.

m.p.: 197° to 198° C.

$[α]_D^{20}$: +35.9° (c=1.00, dimethylformamide)

(4) To 20 ml of a tetrahydrofuran solution containing 1.26 g of propanal was added dropwise 100 ml of a suspension containing 4.50 g of the compound obtained suspended in tetrahydrofuran. The mixture was stirred at room temperature for 3.5 hours. Then, under ice cooling, the reaction mixture was added dropwise to a suspension of sodium triacetoxyborohydride (prepared from 1.48 g of $NaBH_4$ and 8.94 g of acetic acid) in 100 ml of tetrahydrofuran and the mixture was stirred for 1 hour. The whole was concentrated to a quarter amount, and poured into ice water, neutralized and then extracted with chloroform. After the organic layer was washed with water and dried, the solvent was removed. The resulting residue was purified by silica gel column chromatography (solvent: chloroform: methanol (15:1)). The resulting crystals were recrystallized from ethyl acetate to obtain 4.14 g of (+)-2-propylamino-5-[4,5 -di-hydropyridazin-3(2H)-on-6-yl]indane.

m.p.: 137° to 138° C.

$[α]_D^{20}$: +24.1° (c=1.00, $CHCl_3$)

(5) The compound obtained was treated in the same manner as in Example 11 to obtain (+)-2-(N-propyl-N-butyrylamino)-5-[4,5-dihydropyridazin-3(2H)-on-6-yl]indane.

m.p.: 103° to 105° C.

$[α]_D^{20}$: +13.3° (c=1.00, methanol)

Example 90

(+)-2-(N-propyl-N-butyrylamino)-5-[4,5-dihydropyridazin-3(2H)-on-6-yl]indane was treated in the same manner as in Example 40 to obtain (+)-2-(N-propyl-N-butyrylamino)-5-[pyridazin-3(2H)-on-6-yl]indane.

m.p.: 159° to 160° C.

$[α]_D^{20}$: +16.3° (c=1.00, methanol)

Example 91

(1) In 100 ml of tetrahydrofuran was suspended 5.7 g of lithium aluminum hydride, and 150 ml of a solution containing 18.9 g of 2-(propionylamino) indane dissolved in tetrahydrofuran was added dropwise to the suspension. The mixture was refluxed under heating for 2 hours. After cooling, excess lithium aluminum hydride was treated with a saturated ammonium chloride aqueous solution, and insolubles were removed by filtration. The filtrate was concentrated, and chloroform was added to the residue. The mixture was washed with water and dried, and the solvent was removed to obtain 17.5 g of 2-(propylamino) indane.

In 200 ml of tetrahydrofuran were dissolved 17.5 g of the compound obtained and 12.12 g of triethylamine, and 17.8 g of methyl chlorocarbonate was added dropwise to the solution under cooling. After the mixture was stirred at room temperature for 2 hours, tetrahydrofuran was removed, and ethyl acetate was added to the residue. The mixture was washed with water and dried, and the solvent was removed to obtain 21.6 g of 2-(N-methoxycarbonyl-N-propylamino)indane.

IR (neat) $cm^{-1}$: 1660

Mass (m/z): 233 ($M^+$)

(2) Under ice cooling, 59.85 g of anhydrous aluminum chloride was added to 21.6 g of the compound obtained and 300 ml of a dichloromethane solution containing methylsuccinyl chloride (prepared from 24.68 g of methyl hydrogen succinate and 23.75 g of oxalyl chloride). The mixture was stirred at room temperature for 2 hours. The reaction mixture was poured into ice water. The organic layer was collected by separation, washed with water and dried, and the solvent was removed to obtain 33.72 g of 2-(N-methoxycarbonyl-N-propylamino)-5-(3-methoxycarbonylpropionyl)indane.

To 400 ml of a xylene solution containing 33.72 g of the compound obtained were added 12.75 g of hydrazine monohydrate and 24 ml of acetic acid. The mixture was refluxed under heating for 4 hours. The reaction mixture was poured into ice water, extracted with ethyl acetate. After the extract was washed with water and dried, the solvent was removed. The residue was solidified in a mixed solution of diisopropyl ether and hexane to obtain 28.96 g of 2-(N-methoxycarbonyl-N-propylamino)-5-[4,5-dihydropyridazin-3(2H)-on-6-yl]indane.

IR (neat) $cm^{-1}$: 3200, 1680, 1660

Mass (m/z): 329 ($M^+$)

Examples 92 to 9

By treating the corresponding starting compounds in the same manner as in Example 4-(1) and Example 4-(2), compounds shown in Table 15 were obtained.

TABLE 15

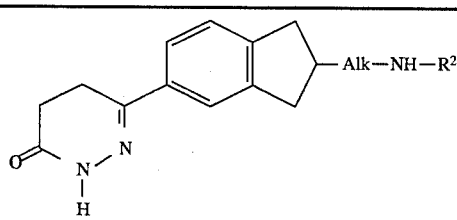

| Example No. | Alk | $R^2$ | Physical properties |
|---|---|---|---|
| 92 | $-CH_2-$ | $-n-C_3H_7$ | the same as those of the compound obtained in Example 9-(1) |
| 93 | $-(CH_2)_2-$ | $-n-C_3H_7$ | the same as those of the compound obtained in Example 10 |
| 94 | $-(CH_2)_3-$ | H | m.p. 163 to 165° C. |
| 95 | $-(CH_2)_3-$ | $-n-C_3H_7$ | m.p. 109 to 110° C. |
| 96 | $-(CH_2)_4-$ | $-n-C_3H_7$ | m.p. 94 to 96° C. |
| 97 | $-(CH_2)_5-$ | H | m.p. 130 to 131° C. |
| 98 | $-(CH_2)_6-$ | H | m.p. 136 to 138° C. |

Examples 99 to 101

By treating the corresponding starting compounds in the same manner as in Example 4-(3), compounds shown in Table 16 were obtained.

TABLE 16

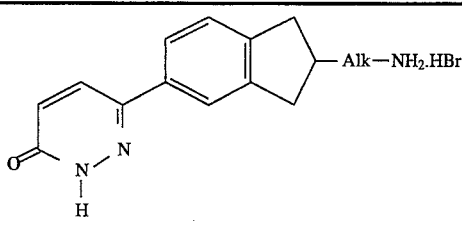

| Example No. | Alk | Physical properties |
|---|---|---|
| 99 | $-(CH_2)_3-$ | m.p. > 300° C. |
| 100 | $-(CH_2)_5-$ | m.p. 282 to 283° C. (decomposed) |
| 101 | $-(CH_2)_6-$ | m.p. 288 to 289° C. (decomposed) |

Examples 102 to 104

By treating the corresponding starting compounds in the same manner as in Example 9-(2), compounds shown in Table 17 were obtained.

TABLE 17

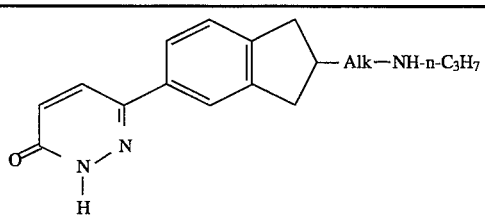

| Example No. | Alk | Physical properties |
|---|---|---|
| 102 | $-(CH_2)_2-$ | m.p. 155 to 156° C. |
| 103 | $-(CH_2)_3-$ | m.p. 157 to 158° C. |
| 104 | $-(CH_2)_4-$ | m.p. 127 to 129° C. |

Examples 105 to 119

By treating the corresponding starting compounds in the same manner as in Example 54, compounds shown in Table 18 were obtained.

TABLE 18

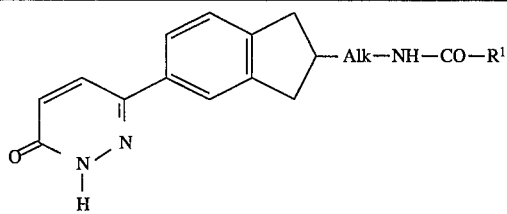

| Example No. | $R^1$ | Alk | Physical properties |
|---|---|---|---|
| 105 | $-CH=CH_2$ | $-(CH_2)_2-$ | m.p. 191 to 192° C. |
| 106 | $-CH=CH_2$ | $-(CH_2)_3-$ | m.p. 161 to 163° C. |
| 107 | $-CH=CH_2$ | $-(CH_2)_5-$ | m.p. 162 to 163° C. |
| 108 | $-CH=CH_2$ | $-(CH_2)_6-$ | m.p. 152 to 154° C. |

TABLE 18-continued

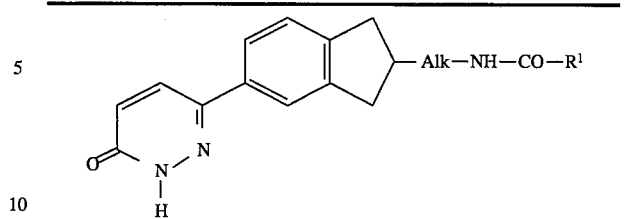

| Example No. | $R^1$ | Alk | Physical properties |
|---|---|---|---|
| 109 | 4-pyridyl | $-(CH_2)_2-$ | m.p. 245 to 246° C. |
| 110 | 3-pyridyl | $-(CH_2)_2-$ | m.p. 172 to 174° C. |
| 111 | 3-pyridyl | $-(CH_2)_3-$ | m.p. 196 to 198° C. |
| 112 | 3-pyridyl | $-(CH_2)_4-$ | m.p. 192 to 193° C. |
| 113 | 3-pyridyl | $-(CH_2)_5-$ | m.p. 155 to 156° C. |
| 114 | 3-pyridyl | $-(CH_2)_6-$ | m.p. 179 to 180° C. |
| 115 | $-CH_3$ | $-(CH_2)_3-$ | m.p. 168 to 170° C. |
| 116 | $-C_2H_5$ | $-(CH_2)_3-$ | m.p. 171 to 172° C. |
| 117 | $-n-C_3H_7$ | $-(CH_2)_3-$ | m.p. 156 to 158° C. |
| 118 | cyclopropyl | $-(CH_2)_3-$ | m.p. 190 to 192° C. |
| 119 | $-CH_2CH(CH_3)_2$ | $-(CH_2)_3-$ | m.p. 189 to 191° C. |

Examples 120 to 122

By treating the corresponding starting compounds in the same manner as in Example 54, compounds shown in Table 19 were obtained.

TABLE 19

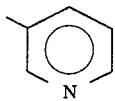

| Example No. | R¹ | R² | Alk | Physical properties |
|---|---|---|---|---|
| 120 | —CH=CH₂ | -n-C₃H₇ | —(CH₂)₂— | m.p. 113 to 115° C. |
| 121 | (3-pyridyl) | -n-C₃H₇ | —(CH₂)₂— | m.p. 110 to 112° C. |
| 122 | —CH=CH₂ | -n-C₃H₇ | —(CH₂)₃— | m.p. 107 to 109° C. |

Examples 123 to 134

By treating the corresponding starting compounds in the same manner as in Example 65, compounds shown in Table 20 were obtained.

TABLE 20

| Example No. | R¹ | Alk | Physical properties |
|---|---|---|---|
| 123 | (3-pyridyl) | —(CH₂)₂— | the same as those of the compound obtained in Example 110 |
| 124 | (pyrazinyl) | —(CH₂)₂— | m.p. 218 to 220° C. |
| 125 | (6-chloro-3-pyridyl) | —(CH₂)₂— | m.p. 205 to 207° C. |
| 126 | (3-methoxy-5-pyridyl) | —(CH₂)₂— | m.p. 177 to 178° C. |
| 127 | (2-methyl-3-pyridyl) | —(CH₂)₂— | m.p. 206 to 208° C. |
| 128 | (3-quinolyl) | —(CH₂)₂— | m.p. 231 to 232° C. |

TABLE 20-continued

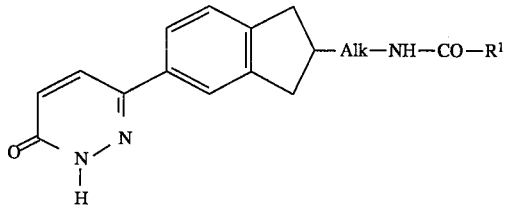

| Example No. | R¹ | Alk | Physical properties |
|---|---|---|---|
| 129 | 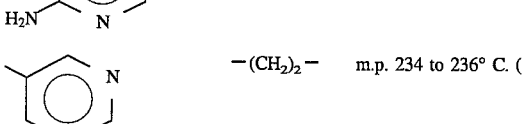 | —(CH$_2$)$_2$— | m.p. 224 to 225° C. |
| 130 | 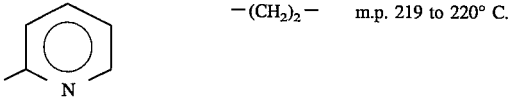 | —(CH$_2$)$_2$— | m.p. 234 to 236° C. (decomposed) |
| 131 | 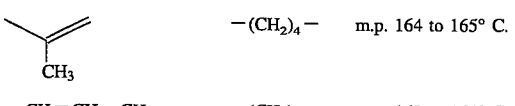 | —(CH$_2$)$_2$— | m.p. 219 to 220° C. |
| 132 | 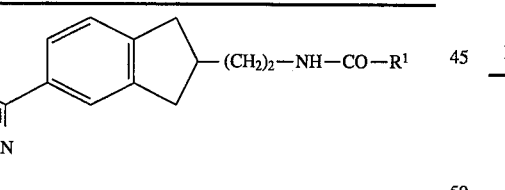 | —(CH$_2$)$_4$— | m.p. 164 to 165° C. |
| 133 | —CH=CH—CH$_3$ | —(CH$_2$)$_4$— | m.p. 162 to 164° C. |
| 134 | —CH=CH—CH=CH$_2$ | —(CH$_2$)$_4$— | m.p. 193 to 195° C. |

Examples 135 to 146

By treating the corresponding starting compounds in the same manner as in Example 65, compounds shown in Table 21 were obtained.

TABLE 21

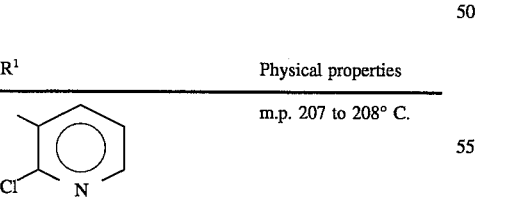

| Example No. | R¹ | Physical properties |
|---|---|---|
| 135 | 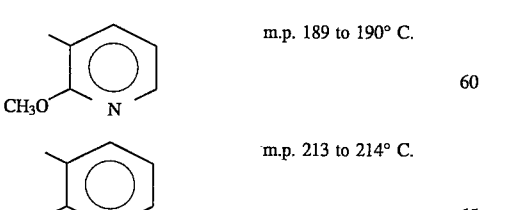 | m.p. 207 to 208° C. |
| 136 | 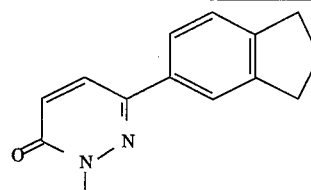 | m.p. 189 to 190° C. |
| 137 | 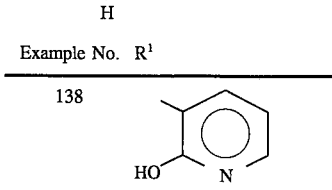 | m.p. 213 to 214° C. |

TABLE 21-continued

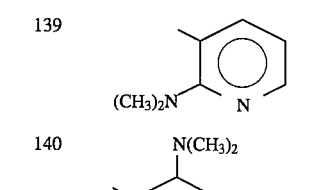

| Example No. | R¹ | Physical properties |
|---|---|---|
| 138 | 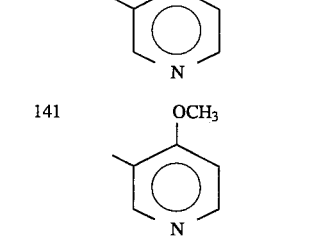 | m.p. 270 to 271° C. |
| 139 | (CH$_3$)$_2$N— pyridyl | m.p. 173 to 175° C. |
| 140 | N(CH$_3$)$_2$ pyridyl | m.p. 237 to 240° C. |
| 141 | OCH$_3$ pyridyl | m.p. 198 to 200° C. (decomposed) |

TABLE 21-continued

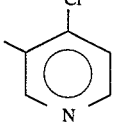

| Example No. | R¹ | Physical properties |
|---|---|---|
| 142 | 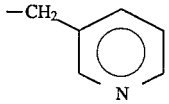 | m.p. 181 to 182° C. |
| 143 | —CH₂— 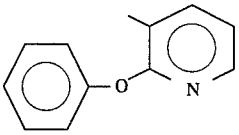 | m.p. 195 to 197° C. |
| 144 | 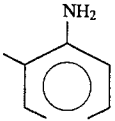 | m.p. 231 to 232° C. |
| 145 | 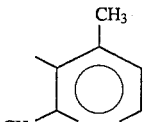 | m.p. 248 to 250° C. (decomposed) |
| 146 | 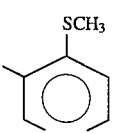 | m.p. 184 to 185° C. |
| 147 | 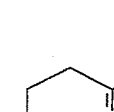 | m.p. 221 to 222° C. |

Examples 148 to 157

By treating the corresponding starting compounds in the same manner as in Example 65, compounds shown in Table 22 were obtained.

TABLE 22

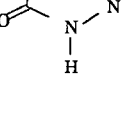

| Example No. | R¹ | Alk | Physical properties |
|---|---|---|---|
| 148 | 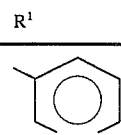 | —(CH₂)₂— | m.p. 171 to 173° C. |
| 149 | 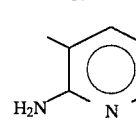 | —(CH₂)₂— | m.p. 190 to 192° C. |
| 150 | 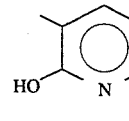 | —(CH₂)₂— | m.p. 247 to 248° C. |
| 151 | 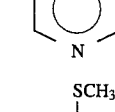 | —(CH₂)₃— | m.p. 161 to 163° C. |
| 152 | 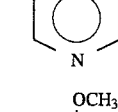 | —(CH₂)₂— | m.p. 191 to 192° C. |
| 153 | 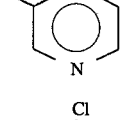 | —(CH₂)₂— | m.p. 148 to 150° C. |
| 154 | 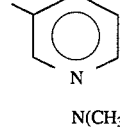 | —(CH₂)₂— | m.p. 171 to 172° C. |
| 155 | 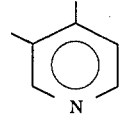 | —(CH₂)₂— | m.p. 201 to 202° C. |
| 156 | 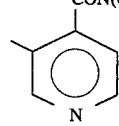 | —(CH₂)₂— | m.p. 167 to 168° C. |

TABLE 22-continued

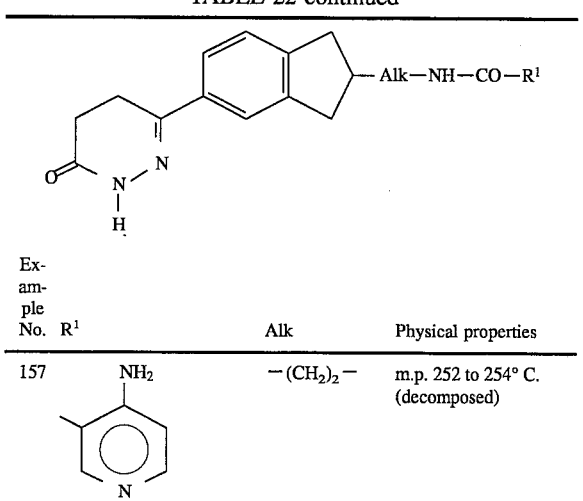

| Example No. | $R^1$ | Alk | Physical properties |
|---|---|---|---|
| 157 | NH$_2$ (4-pyridyl) | —(CH$_2$)$_2$— | m.p. 252 to 254° C. (decomposed) |

Examples 158 and 159

By treating the corresponding starting compounds in the same manner as in Example 68, compounds shown in Table 23 were obtained.

TABLE 23

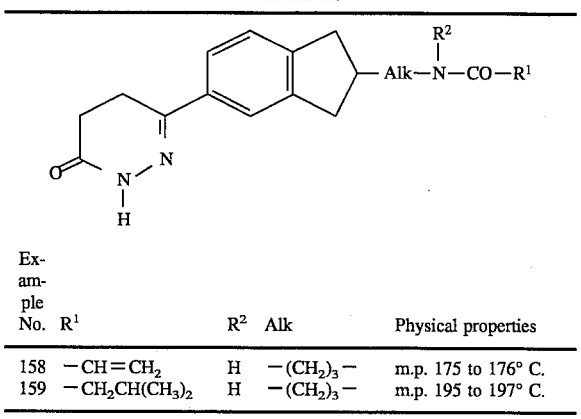

| Example No. | $R^1$ | $R^2$ | Alk | Physical properties |
|---|---|---|---|---|
| 158 | —CH═CH$_2$ | H | —(CH$_2$)$_3$— | m.p. 175 to 176° C. |
| 159 | —CH$_2$CH(CH$_3$)$_2$ | H | —(CH$_2$)$_3$— | m.p. 195 to 197° C. |

The desired indane derivative (I) of the present invention and a pharmaceutically acceptable salt thereof have excellent actions of protecting from endotoxin shock and/or excellent actions of curing nephritis so that they are useful as, for example, an agent for preventing and curing endotoxin shock which occurs in a patient seriously infected with gram-negative bacteria or an agent for preventing and curing nephritis.

Further, the desired compound (I) of the present invention has low toxicity so that it can be a medicine having high safety.

We claim:

1. A method for prophylaxis or treating endotoxin shock and/or nephritis in a patient in need thereof, which comprises administering to said patient a therapeutically effective amount of a compound of the formula:

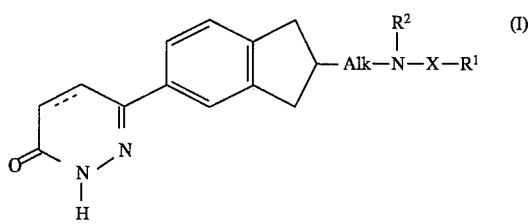

wherein $R^1$ represents a substituted or unsubstituted aryl group, a lower alkyl group, a cycloalkyl group, a halogeno-lower alkyl group, a lower alkenyl group, a phenyl-substituted lower alkenyl group, a substituted or unsubstituted monocyclic or bicyclic aromatic heterocyclic group having a nitrogen atom, oxygen atom or sulfur atom as a hetero atom, a lower alkyl group which is substituted by a substituted or unsubstituted monocyclic or bicyclic aromatic heterocyclic group having a nitrogen atom, oxygen atom or sulfur atom as a hetero atom, a substituted or unsubstituted lower alkoxy group, phenoxy group, a lower alkylamino group, a lower alkenylamino group, phenylamino group or a lower alkenyloxy group; $R^2$ represents a hydrogen atom or a lower alkyl group; X represents a carbonyl group or a thiocarbonyl group; Alk represents a single bonding arm or a lower alkylene group; and the dotted line represents presence or absence of a double bond, or a pharmaceutically acceptable salt thereof.

2. The method according to claim 1, wherein the substituted or unsubstituted aryl group is a phenyl group which may be substituted by 1 to 3 groups selected from the group consisting of a lower alkoxy group, a phenyl-substituted lower alkoxy group, a halogen atom, hydroxyl group, trifluoromethyl group, nitro group, a lower alkyl group and a di-lower alkylamino group; the halogeno-lower alkyl group is trifluoromethyl group; the phenyl-substituted lower alkenyl group is styryl group; the substituted or unsubstituted monocyclic or bicyclic aromatic heterocyclic group having a nitrogen atom, oxygen atom or sulfur atom as a hetero atom is a pyridyl group, a furyl group, a thienyl group, a pyrazyl group, a pyrimidyl group, a quinolyl group or an isoquinolyl group each of which may be substituted by 1 to 4 groups selected from the group consisting of a lower alkyl group, a halogeno lower alkyl group, a lower alkoxy group, a lower alkylthio group, hydroxy group, mercapto group, cyano group, amino group, a lower alkylamino group, a di-lower alkylamino group, acylamino group, a halogen atom, phenoxy group, carboxyl group, a lower alkoxycarbonyl group, a lower alkylcarbonyloxy group, a lower alkylcarbonyl group, carbamoyl group and a di-lower alkylcarbamoyl group; and the substituted or unsubstituted lower alkoxy group is a lower alkoxy group which may be substituted by phenyl group.

3. The method according to claim 1, wherein $R^1$ is a pyridyl group which may be substituted by 1 or 2 groups selected from the group consisting of a lower alkyl group, a halogeno-lower alkyl group, a lower alkoxy group, a lower alkylthio group, hydroxy group, mercapto group, cyano group, amino group, a substituted amino group, a halogen atom, phenoxy group, carboxyl group, a lower alkoxycarbonyl group, a lower alkylcarbonyloxy group, a lower alkylcarbonyl group, carbamoyl group and a di-lower alkylcarbamoyl group; a pyridyl-substituted lower alkyl group; a lower alkyl group; a cycloalkyl group; a lower alkenyl group; or a lower alkoxy group.

4. The method according to claim 1, wherein $R^1$ is pyridyl group which may be substituted by 1 or 2 groups selected from the group consisting of a lower alkyl group and amino group; a lower alkyl group; a lower alkenyl group; or a lower alkoxy group.

5. The method according to claim 1, wherein $R^1$ is pyridyl group which may be substituted by 1 or 2 groups selected from the group consisting of methyl group and amino group.

6. The method according to claim 1, wherein $R^2$ is hydrogen atom.

7. The method according to claim 1, wherein $R^2$ is a lower alkyl group.

8. The method according to claim 1 wherein X is carbonyl group.

9. The method according to claim 1, wherein Alk is a lower alkylene group.

10. The method according to claim 1, wherein the dotted line represents presence of a double bond.

11. The method according to claim 1, wherein $R^1$ is pyridyl group which may be substituted by 1 or 2 groups selected from the group consisting of a lower alkyl group, a halogeno-lower alkyl group, a lower alkoxy group, a lower alkylthio group, hydroxy group, mercapto group, cyano group, amino group, a substituted amino group, a halogen atom, phenoxy group, carboxyl group, a lower alkoxycarbonyl group, a lower alkylcarbonyloxy group, a lower alkylcarbonyl group, carbamoyl group and a di-lower alkylcarbamoyl group; a pyridyl-substituted lower alkyl group; a lower alkyl group; a cycloalkyl group; a lower alkenyl group; or a lower alkoxy group and X is carbonyl group.

12. The method according to claim 1, wherein $R^1$ is pyridyl group which may be substituted by 1 or 2 groups selected from the group consisting of a lower alkyl group and amino group; a lower alkyl group; a lower alkenyl group; or a lower alkoxy group, X is carbonyl group, Alk is a lower alkylene group and the dotted line represents presence of a double bond.

13. The method according to claim 1, wherein $R^1$ is pyridyl group which may be substituted by 1 or 2 groups selected from the group consisting of a lower alkyl group and amino group; a lower alkyl group; a lower alkenyl group; or a lower alkoxy group, $R^2$ is hydrogen atom, X is carbonyl group, Alk is a lower alkylene group and the dotted line represents presence of a double bond.

14. The method according to claim 1, wherein $R^1$ is pyridyl group which may be substituted by 1 or 2 groups selected from the group consisting of methyl group and amino group, $R^2$ is hydrogen atom, X is carbonyl group, Alk is a lower alkylene group and the dotted line represents presence of a double bond.

15. The method according to claim 1, wherein $R^1$ is an aryl group, an aryl group substituted by at least one group selected from the group consisting of a $C_{1-4}$ alkoxy group, a phenyl-substituted $C_{1-4}$ alkoxy group, a halogen atom, a hydroxyl group, a trifluoromethyl group, a nitro group, a $C_{1-4}$ alkyl group and a di-$C_{1-4}$ alkylamino group, an alkyl group having 1 to 4 carbon atoms, a cycloalkyl group having 3 to 6 carbon atoms, a halogeno-alkyl group having 1 to 4 carbon atoms, an alkenyl group having 2 to 5 carbon atoms, a phenyl-substituted alkenyl group having 2 to 5 alkenyl carbon atoms, a monocyclic or bicyclic aromatic heterocyclic group selected from a pyridyl group, a furyl group, a thienyl group, a pyrazyl group, a pyrimidyl group, a quinolyl group and an isoquinolyl group each of which may be substituted by 1 to 4 groups selected from the group consisting of an alkyl group having 1 to 4 carbon atoms, a halogeno-alkyl group having 1 to 4 carbon atoms, an alkoxy group having 1 to 4 carbon atoms, an alkylthio group having 1 to 4 carbon atoms, hydroxy group, mercapto group, cyano group, amino group, a substituted amino group, a halogen atom, phenoxy group, carboxyl group, an alkoxycarbonyl group having 2 to 5 carbon atoms, an alkylcarbonyloxy group having 2 to 5 carbon atoms, an alkylcarbonyl group having 2 to 5 carbon atoms, carbamoyl group and a di-$C_{1-4}$ alkylcarbamoyl group, an alkoxy group having 1 to 4 carbon atoms, a phenyl-substituted alkoxy group having 1 to 4 alkoxy carbon atoms, phenoxy group, an alkylamino group having 1 to 4 carbon atoms, an alkenylamino group having 2 to 5 carbon atoms, phenylamino group or an alkenyloxy group having 2 to 5 carbon atoms; $R^2$ is hydrogen atom or an alkyl group having 1 to 4 carbon atoms; X is carbonyl group or thiocarbonyl group; and Alk is a single bonding arm or an alkylene group having 1 to 6 carbon atoms.

16. The method according to claim 1, wherein $R^1$ is —$CH_3$, —$C_2H_5$, —n—$C_3H_7$, —n—$C_4H_9$, —$CF_3$, —$CH_2CH(CH_3)_2$, cyclopropyl group, —CH=$CH_2$, —CH=CH—$CH_3$, —CH=CH—CH=$CH_2$, —C($CH_3$)=$CH_2$, styryl group, —CH=C($CH_3$)$_2$, pyridylmethyl group, phenyl group, pyridyl group, furyl group, thienyl group, pyrazyl group, pyrimidyl group, quinolyl group, isoquinolyl group, phenoxy group, benzyloxy group, —O—$CH_3$, —O—n—$C_3H_7$, —O—CH=$CH_2$, —O—$CH_2CH(CH_3)_2$, —NH—n—$C_3H_7$, —NH—n—$C_4H_9$, phenyl-amino group or —NH—$CH_2$—CH=$CH_2$; $R^2$ is hydrogen atom or —n—$C_3H_7$; X is carbonyl group or thiocarbonyl group; and Alk is —$CH_2$—, —($CH_2$)$_2$—, —($CH_2$)$_3$—, —($CH_2$)$_4$—, —($CH_2$)$_5$— or —($CH_2$)$_6$—.

17. The method according to claim 1, wherein the compound is at least one selected from the group consisting of 2-butyrylamino-5-[4,5-dihydropyridazin-3(2H)-on-6-yl]-indane, 2-propionylamino-5-[4,5-dihydropyridazin-3(2H)-on-6-yl]indane, 2-(3-pyridylcarbonylamino)-5-[4,5-dihydropyridazin-3(2H)-on-6-yl]indane, 2-(2-pyridylcarbonylamino)-5-[4,5-dihydropyridazin-3(2H)-on-6-yl]indane, 2-(2-pyridylcarbonylamino)-5-[4,5-dihydropyridazin-3(2H)-on-6-yl]indane, 2-(N-propyl-N-isobutoxycarbonylamino)-5-[4,5 -dihydropyradazin-3(2H)-on-6-yl]indane, 2-(N-n-propyl-N-benzyloxycarbonylamino)-5-[4,5-dihydropyridazin-3(2H)-on-6-yl]indane, 2-butyrylamino-5-[pyridazin-3(2H)-on-6-yl]-indane, 2-(n-propoxycarbonylamino)-5-[pyridazin-3(2H)-on-6-yl] indane, 2-(acryloylaminobutyl)-5-[pyridazin-3(2H)-on-6-yl]indane, 2-pyridin-3-ylcarbonylaminomethyl)-5-[pyridazin-3(2H)-on-6-yl]indane, 2-(acryloylaminoethyl)-5-[pyridazin-3(2H)-on-6-yl]indane, 2-(acryloylaminopropyl)-5-[pyridazin-3(2H)-on-6-yl]indane, 2-(pyridin-4-ylcarbonyl-aminoethyl)-5-[pyridazin-3(2H)-on-6-yl]indane, 2-(pyridin-3-ylcarbonylaminoethyl)-5-[pyridazin-3(2H)-on-6-yl]indane, 2-(2-methylpyridin-3-ylcarbonylaminoethyl)-5 [pyridazin-3(2H)-on-6-yl]indane, 2-(2-aminopyridin-3-ylcarbonylaminoethyl)-5-[pyridazin-3(2H)-on-6-yl]indane, 2 -(pyridin-3-ylcarbonylaminoethyl)-5-[4,5-dihydropyridazin-3(2H)-on-6-yl]indane, 2-(N-n-propyl-N-acryloylaminoethyl)-5-[pyridazin-3(2H)-on-6-yl]indane and 2-(N-n-propyl-N-pyridin-3-yl-carbonylaminoethyl)-5-[pyridazin-3(2H)-on-6-yl]indane, and a pharmaceutically acceptable salt thereof.

18. The method according to claim 1, wherein the compound is 2-(Pyridin-3-ylcarbonylaminoethyl)-5-[pyridazin-3(2H)-on-6-yl]indane, 2-(2-methylpyridin-3-ylcarbonylaminoethyl)-5-[pyridazin-3(2H)-on-6-yl]indane,2-(2-aminopyridin-3-ylcarbonylaminoethyl)-5-[pyridazin-3(2H)-on-6-yl]indane, 2-(N-n-propyl-N-pyridin-3-ylcarbonylaminoethyl)-5-[pyridazin-3-(2H)-on-6-yl]indane, or a pharmaceutically acceptable salt thereof.

19. The method according to claim 1, wherein the compound is 2-(Acryloylaminopropyl)-5-[pyridazin-3(2H)-on-6-yl]indane,2-(N-n-propyl-N-acryloylaminopropyl)-5-[pyridazin-3(2H)-on-6-yl]indane, or a pharmaceutically acceptable salt thereof.

* * * * *